US012708598B2

(12) United States Patent
Zhang et al.

(10) Patent No.: US 12,708,598 B2
(45) Date of Patent: Aug. 18, 2026

(54) COMPOSITION FOR CARING FOR A KERATIN MATERIAL

(71) Applicant: L'OREAL, Paris (FR)

(72) Inventors: Mei Zhang, Shanghai (CN); Qingsheng Tao, Shanghai (CN)

(73) Assignee: L'OREAL, Paris (FR)

( * ) Notice: Subject to any disclaimer, the term of this patent is extended or adjusted under 35 U.S.C. 154(b) by 441 days.

(21) Appl. No.: 18/251,973

(22) PCT Filed: Nov. 20, 2020

(86) PCT No.: PCT/CN2020/130562
§ 371 (c)(1),
(2) Date: May 5, 2023

(87) PCT Pub. No.: WO2022/104728
PCT Pub. Date: May 27, 2022

(65) Prior Publication Data

US 2024/0016721 A1 Jan. 18, 2024

(51) Int. Cl.
*A61K 8/73* (2006.01)
*A61K 8/34* (2006.01)
*A61K 8/41* (2006.01)
*A61Q 5/12* (2006.01)
*A61Q 19/00* (2006.01)

(52) U.S. Cl.
CPC .............. *A61K 8/735* (2013.01); *A61K 8/345* (2013.01); *A61K 8/416* (2013.01); *A61Q 5/12* (2013.01); *A61Q 19/00* (2013.01)

(58) Field of Classification Search
None
See application file for complete search history.

(56) References Cited

U.S. PATENT DOCUMENTS 9,439,839 B2 9/2016 Sugawara
10,532,023 B2 1/2020 Rossignol-Castera et al.
10,561,698 B2 2/2020 Mouser
10,849,952 B2 12/2020 Mouser
2004/0022819 A1* 2/2004 Ikemoto .................. A61Q 5/02 424/401
2010/0028391 A1* 2/2010 Okawa ..................... A61K 8/06 424/401
2014/0088040 A1 3/2014 Sugawara
2015/0209264 A1 7/2015 Bonnet et al.
2015/0283055 A1 10/2015 Bonnet et al.
2017/0216194 A1 8/2017 Rossignol-Castera et al.
2017/0354705 A1 12/2017 Mouser
2019/0060186 A1 2/2019 Goutayer et al.
2019/0358136 A1* 11/2019 Linares .................... A61Q 5/12
2020/0069761 A1 3/2020 Mouser
2020/0206111 A1 7/2020 Lee et al.
2021/0046142 A1 2/2021 Mouser

FOREIGN PATENT DOCUMENTS

CN 106109296 A 11/2016
CN 106176286 A 12/2016
CN 110507594 A 11/2019
CN 111265425 A 6/2020
CN 111449985 A 7/2020
CN 111939113 A 11/2020
EP 2 559 708 A1 2/2013
FR 3 064 473 A1 10/2018
FR 3 064 474 A1 10/2018
FR 3 095 345 A1 10/2020
JP 08-53501 A 2/1996
JP 2000095647 A * 4/2000
JP 2012-250970 A 12/2012
KR 10-1891951 B1 8/2018
KR 10-2049698 B1 1/2020
WO WO 2011/070620 A1 6/2011
WO WO 2014/064391 A1 5/2014

OTHER PUBLICATIONS

Machine Translation of JP2000095647 (Year: 2000).*
Machine Translation of CN106109296 (Year: 2016).*
International Search Report & Written Opinion issued Aug. 25, 2021 in PCT/CN2020/130562 filed on Nov. 20, 2020, citing documents 1-5 & 12-13 therein, 9 pages.
Preliminary French search Report issued Oct. 14, 2021, citing documents 6-10 & 14-22 therein, 5 pages (with English Translation of Categories of Cited Documents).
Extended European Search Report dated Jun. 26, 2024 in corresponding European Patent Application No. 20962019.4, citing documents 15, 16, 24, 25, 26 and 27 therein, 10 pages.
Mintel; Oct. 13, 2020, "Treatment", XP093172058, Database accession No. 8182571, 2 pages.
Mintel; Jul. 29, 2020, "Treatment S", XP093172062, Database accession No. 7989327, 3 pages.
Mintel; Sep. 30, 2020, "Hyaluronic Serum", XP093172060, Database accession No. 8158371, 9 pages.
Mintel; Jun. 18, 2020, "Serum", XP093172064, Database accession No. 7864569, 5 pages.
Japanese Office Action issued Mar. 4, 2025, in corresponding Japanese Patent Application No. 2023-527080 (with English Translation), 12 pages.
Japanese Office Action issued Aug. 5, 2024 in Japanese Application No. 2023-527080 with English translation, citing document Nos. 15-17 and 24-25 therein, 11 pgs.
Oka, Takashi, Polymers, 2006, vol. 55, No. 10, pp. 802-805, 4 pgs.
Oka, Takashi, et al., Materials Life, vol. 12, No. 4, 2000, pp. 184-188, 5 pgs.

(Continued)

*Primary Examiner* — Jennifer A Berrios
(74) *Attorney, Agent, or Firm* — Oblon, McClelland, Maier & Neustadt, L.L.P.

(57) ABSTRACT

A transparent anhydrous composition for caring for a keratin material comprises: a) at least one acetylated hyaluronic acid or its salt; and b) propylene glycol. And a non-therapeutic process for caring for a keratin material comprises applying the composition onto the keratin material.

11 Claims, No Drawings

(56) References Cited

OTHER PUBLICATIONS

Combined Chinese Office Action and Search Report issued Feb. 27, 2025, in corresponding Chinese Patent Application No. 202080107308.X (with English Translation of Category of Cited Documents) citing documents 1 and 2 therein, 8 pages.

* cited by examiner

COMPOSITION FOR CARING FOR A KERATIN MATERIAL

TECHNICAL FIELD

The present invention relates to a composition for caring for a keratin material and use thereof. In particular, the present invention relates to a transparent anhydrous composition for caring for a keratin material. The present invention also relates to a non-therapeutic process for caring for a keratin material.

BACKGROUND ART

Keratin materials such as the hair and the skin are generally damaged and weakened by the action of external environment such as light and weather.

There are many products available for conditioning the hair or caring for the skin.

WO 2012089797A2 discloses a composition for moisturizing a keratinous material comprising (a) at least one alkoxysilane having at least one solubilizing functional group and at least one amino substituent; (b) at least one glycosaminoglycan chosen from hyaluronic acid, its derivatives and its salts; and (c) water.

WO2003105798A1 discloses a cosmetic emulsion for care and/or makeup, comprising an aqueous phase and a liquid fatty phase dispersed one within the other, said liquid fatty phase comprising at least one silicone oil and being structured with at least one gelling polymer (homopolymer or copolymer) with a weight-average molecular mass ranging from 500 to 500,000, containing at least one moiety comprising: at least one polyorganosiloxane group, composed of 1 to 1000 organosiloxane units in the chain of the moiety or in the form of a graft, and, at least two groups capable of establishing hydrogen interactions chosen from among the ester, amide, sulfonamide, carbamate, thiocarbamate, urea, thiourea, oxamido, guanidino, biguanidino groups, and combinations thereof, on condition that at least one of the groups is other than an ester group, the polymer being solid at room temperature and soluble in the liquid fatty phase at a temperature of from 25° C. to 250° C., the aqueous phase, the liquid fatty phase and the gelling polymer forming a physiologically acceptable medium.

During the development of cosmetic products, it is highly desirable to provide some products with pleasant appearance, for example, some product with transparent appearance.

It is also desirable that the products are stable over time.

Hyaluronic acid is known for its film-forming and water-retaining power. Hyaluronic acid is a predominant glycosaminoglycan located in the skin. This compound and the salts thereof are conventionally used in cosmetics for their hygroscopic, viscoelastic and rheological properties, advantageously making it possible to moisturize and plump up the skin, and to reduce wrinkles and dehydration lines, with anti-aging effects. The hyaluronic acids most commonly used for the abovementioned applications are macro molecules of a molecular weight of between 500 kDa and 2 000 kDa. Indeed, it has been demonstrated that supplying these high-molecular-weight hyaluronic acids provides an effective moisturizing effect to the skin, by virtue of their hygroscopic properties which are characteristic of these molecules.

However, there is no commercial product comprising hyaluronic acid or its derivative in an anhydrous system, which is transparent and stable over time.

SUMMARY OF THE INVENTION

An object of the present invention is thus to develop a composition containing hyaluronic acid or its derivative in an anhydrous system, which is transparent and stable over time.

Thus, according to a first aspect, the present invention provides a transparent anhydrous composition for caring for a keratin material comprising:

a) at least one acetylated hyaluronic acid or its salt; and b) propylene glycol.

According to a second aspect, the present invention provides a non-therapeutic process for caring for a keratin material comprising applying the composition as described above onto the keratin material.

The inventors have found that the composition has a transparent appearance and is stable over time, and the composition is effective in caring for a keratin material.

Other subjects and characteristics, aspects and advantages of the present invention will emerge even more clearly on reading the detailed description and the examples that follow.

DETAILED DESCRIPTION OF THE INVENTION

As used herein, unless otherwise indicated, the limits of a range of values are included within this range, in particular in the expressions "between . . . and . . . " and "from . . . to . . . ".

As used herein, the term "comprising" is to be interpreted as encompassing all specifically mentioned features as well optional, additional, unspecified ones.

As used herein, the use of the term "comprising" also discloses the embodiment wherein no features other than the specifically mentioned features are present (i.e. "consisting of").

Unless otherwise defined, all technical and scientific terms used herein have the same meaning as commonly understood by those skilled in the field the present invention belongs to. When the definition of a term in the present description conflicts with the meaning as commonly understood by those skilled in the field the present invention belongs to, the definition described herein shall apply.

Unless otherwise specified, all numerical values expressing amount of ingredients and the like used in the description and claims are to be understood as being modified by the term "about". Accordingly, unless indicated to the contrary, the numerical values and parameters described herein are approximate values which are capable of being changed according to the desired performance obtained as required.

As used therein, the term "keratin material" includes animal keratin material and human keratin material such material as the hair and the skin.

As used herein, the expression "at least one" used in the present description is equivalent to the expression "one or more".

By "anhydrous", it means that no water is added on purpose and the water content of the composition is less than 0.5 wt. %, particularly less than 0.1 wt. %, relative to the total weight of the composition. In particular, there is no water in the composition.

According to the first aspect of the present invention, a transparent anhydrous composition for caring for a keratin material comprises:

a) at least one acetylated hyaluronic acid or its salt; and b) propylene glycol.

Acetylated Hyaluronic Acid or its Salt

Acetylated hyaluronic acid is a derivative obtained by a process comprising substituting a hydroxyl on the disaccharide structure of hyaluronic acid (HA). The structure of acetylated hyaluronic acid is as follows:

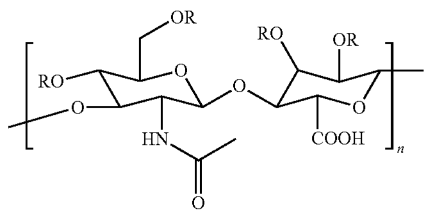

wherein each R is independently CH 3 CO— or H, at least one R is CH 3 CO—.

Salts of acetylated hyaluronic acid include acetylated sodium hyaluronate, acetylated potassium hyaluronate.

The structure of acetylated sodium hyaluronate is as follows:

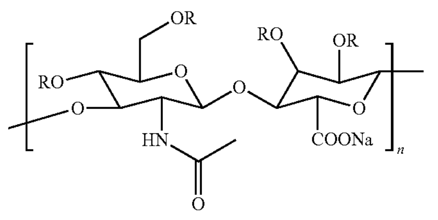

wherein each R is independently CH 3 CO— or H, at least one R is CH 3 CO—.

The acetylation degree (proportion of acetylation-modified hyaluronic acid) of the acetylated hyaluronic acid can be determined by NMR. It is preferable that the acetylated hyaluronic acid or its salt has an acetylation degree of from 0.5 to 1. It is more preferable that the acetylated hyaluronic acid or its salt has an acetylation degree of from 0.75 to 1, even from 0.8 to 1.

It is preferable that the acetylated hyaluronic acid or its salt has a weight average molecular weight of from 1,000 Da to 100,000 Da, as determined by liquid chromatography (HPLC) method. It is more preferable that the acetylated hyaluronic acid or its salt has a weight average molecular weight from 20,000 Da to 50,000 Da, even Da to 30,000 Da as determined by liquid chromatography (HPLC) method.

Two or more kinds of acetylated hyaluronic acids or its salts having different weight average molecular weights may be used together.

As commercial products of the acetylated hyaluronic acid or its salt, mention can be made of that sold under the name HYMAGIC-ACHA by the company BLOOMAGE FREDA BIOPHARM, which is acetylated sodium hyaluronate with an acetylation degree of and a weight average molecular weight of 30000 to 50000 Da, and that sold under the name PRIMALHYAL ULTRAFILLER by the company GIVAUDAN, which is acetylated sodium hyaluronate with an acetylation degree of 1 and a weight average molecular weight of 20000 Da.

Advantageously, the acetylated hyaluronic acid or its salt is present in amount ranging from 0.01 wt. % to 20 wt. %, preferably from 0.1 wt. % to 10 wt. %, more preferably from 0.3 wt. % to 5 wt. %, relative to the total weight of the composition.

Propylene Glycol

According to the first aspect, the composition of the present invention comprises propylene glycol.

In the present invention, the definition of propylene glycols includes all possible isomers, 1,3-propylene glycol, 1,2-propylene glycol and 1,1-propylene glycol.

Advantageously, propylene glycol is present in an amount ranging from 10 wt. % to wt. %, preferably from 30 wt. % to 95 wt. %, preferably from 40 wt. % to 95 wt. %, relative to the total weight of the composition.

Cationic Surfactants

In some embodiments, the composition according to the present invention comprises a cationic surfactant.

The term "cationic surfactant" means a surfactant that may be positively charged when it is contained in the composition according to the present invention. This surfactant may bear one or more positive permanent charges or may contain one or more functional groups that are cationizable in the composition according to the disclosure.

Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamidopropyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some instances, the cationic surfactant is preferably selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some instances, the cationic surfactant is more preferably selected from cetrimonium chloride, behentrimonium chloride, behentrimonium methosulfate, stearamidopropyl dimethylamine, and a mixture thereof.

Moreover, in some cases, the cationic surfactant is most preferably cetrimonium chloride, behentrimonium chloride, or a mixture thereof.

If presents, the cationic surfactant is present in an amount ranging from 0.1 wt. % to 5 wt. %, relative to the total weight of the composition.

Additional Alcohols

In some embodiments, the composition according to the present invention further comprises an additional alcohol in addition to propylene glycol, for example monoalcohol having from 2 to 6 carbon atoms, ethylene glycol, butylene glycol, pentylene glycol, and glycerin.

For example, the monoalcohol may be selected from ethanol, propanol, butanol, pentanol, hexanol, isopropyl alcohol, cycohexanol, isobutyl alcohol, 2-methyl-2-butanol (2-methylbutan-2-ol), and a mixture thereof.

In some instances, the one or more monoalcohls include ethanol. For example, the compositions may include ethanol and optionally one or more additional monoalcohols having from 2 to 6 carbon atoms.

If presents, the additional alcohol is present in an amount ranging from 5 wt. %, to 95 wt. %, preferably from 20 wt. % to 50 wt. %, relative to the total weight of the composition.

Additional Cosmetic Active Ingredients

In some embodiments, the composition according to the present invention comprises at least one cosmetic active ingredient for caring for the keratious materials.

The cosmetic active ingredient can dissolve in the anhydrous medium, especially propylene glycol.

As examples of the cosmetic active ingredient can be contained in the composition according to the present invention, mention can be made of *Polygonum cuspidatum* root extract, ascorbic acid, ferulic acid, caffeine, nicotinamide, panthenol, ceramide, amino acid, etc.

The skilled in the art can adjust the amount of the cosmetic active ingredient depending on the intended purpose.

Additional Adjuvants or Additives

The composition of the present invention may comprise conventional cosmetic adjuvants or additives, for instance fragrances, chelating agents (for example, disodium EDTA), preserving agents (for example, chlorphenesin and phenoxyethanol) and bactericides, surfactants, thickeners, pH regulators (for example citric acid, sodium hydroxide, potassium hydroxide), and mixtures thereof.

The skilled in the art can select the amount of the additional adjuvants or additive so as not to adversely impact the final use of the composition according to the present invention.

Preparation and Use

The composition according to the present invention can be prepared by mixing ingredients a) and b), as essential ingredients, as well as additional ingredient(s), as explained above.

The method and means to mix the above essential and optional ingredients are not limited. Any conventional method and means can be used to mix the above essential and optional ingredients to prepare the composition according to the present invention.

The composition according to the present invention has a transparent appearance.

The term "transparent" means that the composition has a turbidity of less than or equal to 20 NTU (nephelometric turbidity units). The turbidity measurement may be carried out, for example, with a WGZ-200B turbidimeter from Shanghai INESA Physico-optical instrument Co., Ltd. The measurements are carried out at ambient temperature (20° C. to 25° C.).

Preferably, the composition of the present invention may have a turbidity less than or equal to 10 NTU, and preferably less than or equal to 5 NTU, and even more preferably less than or equal to 2 NTU.

The composition according to the present invention is stable over time.

"Stable over time" is understood to mean the composition of the present invention which, after storage at all temperatures between 4° C. and 45° C. for 2 months, does not exhibit any variation in microscopic appearance.

Preferably, the transparent appearance of the composition according to the present invention is stable over time.

The composition according to the present invention can be used as rinse-off or leave-on products, such as conditioners for the hair, or skincare products.

According to the second aspect of the present invention, a non-therapeutic process for caring for a keratin material comprising applying the composition as described above onto the keratin material.

In some embodiments, the transparent anhydrous composition according to the present invention is intended for caring for the hair, so as to remain the hair firm, shiny and bouncy.

In some embodiments, the transparent anhydrous composition according to the present invention is intended for moisturisation of the skin, so as to provide hydration effect on the skin.

The following examples are given by way of illustration of the present invention and shall not be interpreted as limiting the scope.

EXAMPLES

Main raw materials used, trade names and supplier thereof are listed in Table 1.

TABLE 1

| INCI Name | Trade Name | Supplier |
|---|---|---|
| Propylene glycol | MONOPROPYLENE GLYCOL | DONGYING HI-TECH SPRING CHEMICAL IN |
| Butylene glycol | 1,3 BUTYLENE GLYCOL | ALZO |
| Dipropylene glycol | DIPROPYLENE-GLYCOL | INEOS |
| Glycerin | REFINED GLYCERIN | RENOVA |
| Dicaprylyl carbonate | CETIOL ® CC | BASF |
| Cetrimonium chloride | DEHYQUART ® A-OR | BASF |
| Ethanol | ABSOLUTE ETHANOL | ANHUI ANTE FOOD |
| Myristyl alcohol | LANETTE 14 | BASF |
| Behentrimonium chloride | BTAC P7580KC | KCI |

TABLE 1-continued

| INCI Name | Trade Name | Supplier |
|---|---|---|
| Acetylated sodium hyaluronate | PRIMALHYAL ™ ULTRAFILLER | GIVAUDAN |
| Polygonum cuspidatum root extract | POLYGONUM CUSPIDATUM ROOT EXTRACT | GUILIN LAYN NATURAL INGREDIENTS |
| Ascorbic acid | ASCORBIC ACID 100 MESH | CSPC WEISHENG PHARMACEUTICAL |
| Ferulic acid | ORYZA FERULIX | ORYZA OIL & FAT CHEMICAL |
| Sodium hyaluronate (Mw > 100 kDa) | CRISTALHYAL'LO | SOLIANCE (GIVAUDAN) |
| Sodium hyaluronate (Mw = 20-50 kDa) | RENOVHYAL LO | SOLIANCE (GIVAUDAN) |
| Hydrolyzed sodium hyaluronate (Mw < 5 kDa) | MICROHA ™ SUPER ACTIVE HYALURONIC ACID | BLOOMAGE FREDA BIOPHARM |
| Sodium hyaluronate (Oil dispersed HA) | HYACOLOR ™-LA | BLOOMAGE FREDA BIOPHARM |

Invention Examples 1-4 and Comparative Examples 1-2

Hair conditioners of invention formulas (IE.) 1-4 and comparative formulas (CE.) 1-4 were prepared with the ingredients listed in Table 2 (the contents are expressed as parts by weight, unless otherwise indicated):

TABLE 2

| INCI name | IE. 1 | IE. 2 | IE. 3 | IE. 4 | CE. 1 | CE. 2 | CE. 3 | CE. 4 |
|---|---|---|---|---|---|---|---|---|
| | Part by weight | | | | | | | |
| Propylene glycol | 93.95 | 73.95 | 73.95 | 73.95 | — | — | — | — |
| Butylene glycol | — | — | — | — | 93.95 | — | — | — |
| Dipropylene glycol | — | — | — | — | — | 93.95 | — | — |
| Glycerin | — | — | — | — | — | — | 93.95 | — |
| Ethanol | — | 20 | 20 | 20 | — | — | — | 93.95 |
| Dicaprylyl carbonate | 0.9 | 0.9 | 0.9 | 0.9 | 0.9 | 0.9 | 0.9 | 0.9 |
| Cetrimonium chloride | 2.4 | 2.4 | 2.4 | 2.4 | 2.4 | 2.4 | 2.4 | 2.4 |
| Myristyl alcohol | 2 | 2 | 2 | 2 | 2 | 2 | 2 | 2 |
| Behentrimonium chloride | 0.75 | 0.75 | 0.75 | 0.75 | 0.75 | 0.75 | 0.75 | 0.75 |
| Acetylated sodium hyaluronate | 10 | 1 | 10 | 20 | 10 | 10 | 10 | 10 |

Hair conditioner of invention formulas 1-4 comprise propylene glycol and acetylated sodium hyaluronate.

Hair conditioner of comparative formula 1 comprises butylene glycol instead of propylene glycol.

Hair conditioner of comparative formula 2 comprises dipropylene glycol instead of propylene glycol.

Hair conditioner of comparative formula 3 comprises glycerin instead of propylene glycol.

Hair conditioner of comparative formula 4 comprises ethanol instead of propylene glycol.

Preparation Procedure:

The hair conditioners were prepared as follows, with the hair conditioner of invention formula 2 as example:

1). Mix propylene glycol, myristyl alcohol, dicaprylyl carbonate, cetrimomium chloride, if present, and behentrimonium chloride under 60° C. to get a haircare glycol phase;

2). Add acetylated sodium hyaluronate, if presents, into the glycol phase;

3). After cooling down to room temperature, mix alcohol with glycol phase directly to obtain a final solution.

Evaluation:

The appearance of each hair conditioner obtained was observed with naked eyes.

The stability of each hair conditioner obtained was evaluated by maintaining the hair conditioner at 4° C., room temperature (20° C.), or 45° C. for 2 months and observing with naked eyes to check whether the hair conditioner is transparent. It will be evaluated as stable if the hair conditioner tested is transparent under all of 4° C., room temperature (20° C.), and 45° C. for 2 months, otherwise, it will be evaluated as unstable.

The turbidity was measured with a WGZ-200B turbidimeter from Shanghai INESA Physico-optical instrument Co., Ltd.

The results were summarized in Table 3.

TABLE 3

| | Properties | | | | | | | |
|---|---|---|---|---|---|---|---|---|
| | IE. 1 | IE. 2 | IE. 3 | IE. 4 | CE. 1 | CE. 2 | CE. 3 | CE. 4 |
| | Appearance | | | | | | | |
| | Transparent | | | | Opaque | | | |
| | Stability | | | | | | | |
| | Stable | | | | instable | | | |
| Turbidity (NTU) | 0.96 | 1.03 | 1.31 | 1.53 | 38348 (>200) | 77.45 | 64338 (>200) | 77060 (>200) |

Invention Examples 5-7 and Comparative Examples 5-8

Skincare serums of invention formulas (IE.) 5-7 and comparative formulas (CE.) 5-8 were prepared with the ingredients listed in Table 4 (the contents are expressed as parts by weight, unless otherwise indicated):

TABLE 4

| INCI name | IE. 5 | IE. 6 | IE. 7 | CE. 5 | CE. 6 | CE. 7 | CE. 8 |
|---|---|---|---|---|---|---|---|
| | Parts by weight | | | | | | |
| Glycerin | 24.37 | 24.37 | 24.37 | 24.37 | 24.37 | 24.37 | 24.37 |
| Polygonum cuspid atum root extract | 0.5 | 0.5 | 0.5 | 0.5 | 0.5 | 0.5 | 0.5 |
| Ascorbic acid | 12.63 | 12.63 | 12.63 | 12.63 | 12.63 | 12.63 | 12.63 |
| Ferulic acid | 1.9 | 1.9 | 1.9 | 1.9 | 1.9 | 1.9 | 1.9 |
| Propylene glycol | 43.5 | 43.5 | 43.5 | 43.5 | 43.5 | 43.5 | 43.5 |
| Dipropylene glycol | 17.1 | 17.1 | 17.1 | 17.1 | 17.1 | 17.1 | 17.1 |
| Sodium acetylated hyaluronate | 5 | 2 | 1 | | | | |
| Sodium Hyaluronate (Mw > 100 kDa) | — | — | — | 0.1 | — | — | — |
| Sodium Hyaluronate (Mw = 20-50 kDa) | — | — | — | — | 0.1 | — | — |
| Hydrolyzed sodium hyaluronate (Mw < 5 kDa) | — | — | — | — | — | 0.1 | — |
| Sodium Hyaluronate (Oil dispersed HA) | — | — | — | — | — | — | 0.1 |

Skincare serum of invention formulas 5-7 comprise propylene glycol and acetylated sodium hyaluronate.

Skincare serum of comparative formula 5 comprises sodium hyaluronate instead of sodium acetylated hyaluronate.

Skincare serum of comparative formula 6 comprises sodium hyaluronate instead of sodium acetylated hyaluronate.

Skincare serum of comparative formula 7 comprises hydrolyzed sodium hyaluronate instead of sodium acetylated hyaluronate.

Skincare serum of comparative formula 8 comprises sodium hyaluronate instead of sodium acetylated hyaluronate.

Preparation Procedure:

The skincare serums were prepared as follows, with the skincare serum of comparative formula 5 as example:

1). Mix glycerin, *Polygonum cuspidatum* root extract, ascorbic acid, ferulic acid, propylene glycol, dipropylene glycol, sodium acetylated hyalutonate, if present, to get a skincare glycol phase;

2). Then heat the glycol phase up to 80° C. and mix for 20 minutes to obtain a solution;

3). Cool the solution to room temperature directly.

Evaluation:

The appearance of each skincare serum obtained was observed with naked eyes.

The stability of each skincare serum obtained was evaluated by maintaining the skincare serum at 4° C., room temperature (20° C.), or 45° C. for 2 months and observing with naked eyes to check whether the skincare serum is transparent. It will be evaluated as stable if the skincare serum tested is transparent under all of 4° C., room temperature (20° C.), and 45° C. for 2 months, otherwise, it will be evaluated as unstable.

The turbidity was measured with a WGZ-200B turbidimeter from Shanghai INESA Physico-optical instrument Co., Ltd.

The results were summarized in Table 5.

TABLE 5

| | Properties | | | | | | |
|---|---|---|---|---|---|---|---|
| | IE. 5 | IE. 6 | IE. 7 | CE. 5 | CE. 6 | CE. 7 | CE. 8 |
| | Appearance | | | | | | |
| | Transparent | | | Opaque | | | |
| | Stability | | | | | | |
| | Stable | | | Instable | | | |
| Turbidity(NTU) | 0.53 | 0.81 | 0.22 | 165.3 | 207.8 (>200) | 101.2 | 120.5 |

The invention claimed is:

1. A composition for caring for a keratin material comprising:

a) from 0.01 wt. % to 20 wt. %, relative to the total weight of the composition of an acetylated hyaluronic acid salt; and b) from 40 wt. % to 95 wt. %, relative to the total weight of the composition of propylene glycol, wherein the composition is anhydrous and transparent.

2. The composition according to claim 1, wherein the salt of acetylated hyaluronic acid is selected from acetylated sodium hyaluronate, acetylated potassium hyaluronate, and a mixture thereof.

3. The composition according to claim 1, wherein the acetylated hyaluronic acid salt has an acetylation degree of from 0.5 to 1.

4. The composition according to claim 1, wherein the acetylated hyaluronic acid salt has a weight average molecular weight of from 1,000 Da to 100,000 Da as determined by liquid chromatography method.

5. The composition according to claim 1, wherein the acetylated hyaluronic acid salt is present in an amount ranging from 0.3 wt. % to 5 wt. % relative to the total weight of the composition.

6. The composition according to claim 1, further comprising at least one cationic surfactant.

7. The composition according to claim 6, wherein the at least one cationic surfactant is selected from the group consisting of cetrimonium chloride, behentrimonium chloride, behentrimonium methosulfate, stearamidopropyl dimethylamine, and a mixture thereof.

8. The composition according to claim 6, wherein the at least one cationic surfactant is present in an amount ranging from 0.1 wt. % to 5 wt. %, relative to the total weight of the composition.

9. A hair conditioner or a skincare product, comprising the composition according to claim 1.

10. A non-therapeutic process for caring for a keratin material comprising applying a composition as defined in claim 1 onto said keratin material.

11. The process according to claim 10, wherein the keratin material is skin or hair.

* * * * *